(12) United States Patent
Chen

(10) Patent No.: US 7,963,942 B2
(45) Date of Patent: Jun. 21, 2011

(54) MEDICAL BALLOONS WITH MODIFIED SURFACES

(75) Inventor: John Jianhua Chen, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 639 days.

(21) Appl. No.: 11/533,588

(22) Filed: Sep. 20, 2006

(65) Prior Publication Data

US 2008/0097302 A1    Apr. 24, 2008

(51) Int. Cl.
*A61M 31/00* (2006.01)
(52) U.S. Cl. .................................. 604/103.14
(58) Field of Classification Search ............. 604/103.07
See application file for complete search history.

(56) References Cited

U.S. PATENT DOCUMENTS

| | | |
|---|---|---|
| 4,490,421 A | 12/1984 | Levy |
| 4,963,313 A | 10/1990 | Noddin et al. |
| 5,047,045 A | 9/1991 | Arney et al. |
| 5,195,969 A | 3/1993 | Wang et al. |
| 5,270,086 A | 12/1993 | Hamlin |
| 5,348,538 A | 9/1994 | Wang et al. |
| 5,366,442 A | 11/1994 | Wang et al. |
| 5,403,340 A | 4/1995 | Wang et al. |
| 5,447,497 A | 9/1995 | Sogard et al. |
| 5,490,839 A * | 2/1996 | Wang et al. ............. 604/103.14 |
| 5,556,383 A | 9/1996 | Wang et al. |
| 5,609,629 A | 3/1997 | Fearnot et al. |
| 5,693,014 A | 12/1997 | Abele et al. |
| 5,746,745 A | 5/1998 | Abele et al. |
| 5,759,172 A | 6/1998 | Weber et al. |
| 5,766,618 A | 6/1998 | Laurencin et al. |
| 5,830,182 A | 11/1998 | Wang et al. |
| 5,945,153 A | 8/1999 | Dearnaley |
| 5,951,941 A | 9/1999 | Wang et al. |
| 6,120,260 A | 9/2000 | Jirele |
| 6,171,278 B1 | 1/2001 | Wang et al. |
| 6,171,287 B1 | 1/2001 | Lynn et al. |
| 6,290,721 B1 | 9/2001 | Heath |
| 6,335,029 B1 | 1/2002 | Kamath et al. |
| 6,406,457 B1 | 6/2002 | Wang et al. |
| 6,432,134 B1 | 8/2002 | Anson et al. |
| 6,517,888 B1 | 2/2003 | Weber |
| 6,531,182 B2 | 3/2003 | Veerasamy et al. |
| 6,562,445 B2 | 5/2003 | Iwamura |
| 6,720,402 B2 | 4/2004 | Langer et al. |
| 6,726,712 B1 | 4/2004 | Raeder-Devens et al. |
| 6,753,071 B1 | 6/2004 | Pacetti |

(Continued)

FOREIGN PATENT DOCUMENTS

EP    0 302 717    2/1989

(Continued)

OTHER PUBLICATIONS

Brückner et al., "Metal plasma immersion ion implantation and deposition (MPIIID): chromium on magnesium", Suface and Coatings Technology, vol. 103-104, pp. 227-230, 1998.

(Continued)

*Primary Examiner* — Nicholas D Lucchesi
*Assistant Examiner* — Pritesh Patel
(74) *Attorney, Agent, or Firm* — Vidas, Arrett & Steinkraus

(57) ABSTRACT

Medical balloons are described that have modified regions that enhance folding of the balloon.

24 Claims, 8 Drawing Sheets

U.S. PATENT DOCUMENTS

| | | |
|---|---|---|
| 6,908,506 B2 | 6/2005 | Zimmermann |
| 6,951,675 B2 | 10/2005 | Chin et al. |
| 6,953,594 B2 | 10/2005 | Lee et al. |
| 2002/0004060 A1 | 1/2002 | Heublein et al. |
| 2002/0082638 A1 | 6/2002 | Porter et al. |
| 2003/0104028 A1 | 6/2003 | Hossainy et al. |
| 2003/0144683 A1 | 7/2003 | Sirhan et al. |
| 2003/0163148 A1 | 8/2003 | Wang et al. |
| 2003/0221307 A1 | 12/2003 | Kaese et al. |
| 2004/0225318 A1 | 11/2004 | Eidenschink et al. |
| 2005/0010275 A1 | 1/2005 | Sahatjian et al. |
| 2005/0015046 A1 | 1/2005 | Weber et al. |
| 2005/0177130 A1 | 8/2005 | Konstantino et al. |
| 2006/0079863 A1 | 4/2006 | Burgmeier et al. |
| 2006/0182873 A1 | 8/2006 | Klisch et al. |
| 2007/0050007 A1 | 3/2007 | Kondyurin et al. |
| 2007/0191923 A1* | 8/2007 | Weber et al. .......... 623/1.11 |
| 2007/0191931 A1 | 8/2007 | Weber et al. |

FOREIGN PATENT DOCUMENTS

| | | |
|---|---|---|
| EP | 0 567 285 | 10/1993 |
| EP | 0 592 320 A2 | 4/1994 |
| EP | 0 876 821 | 11/1998 |
| GB | 2 287 473 | 9/1995 |
| JP | 59-192366 | 10/1984 |
| JP | 60-135062 | 7/1985 |
| WO | WO 01/43790 | 6/2001 |
| WO | WO 03/037223 | 5/2003 |
| WO | 2005/025648 A2 | 3/2005 |
| WO | 2007/098330 A2 | 8/2007 |
| WO | 2007/123627 A1 | 11/2007 |

OTHER PUBLICATIONS

Curriculum Vitae of Dr. Alexey Kondyurin, including, "Ion Beam Treatment of Polymers (IBT)", downloaded Nov. 3, 2005, 27 pp.

R. Günzel, "Integrated high voltage modulator for plasma immersion ion implantation", J. Vac. Sci. Technol. B, vol. 17, No. 2, pp. 895-899, Mar./Apr. 1999.

Günzel et al., "Basic investigations of an integrated modulator for plasma immersion ion implantation", Surface and Coatings Technology, vol. 136, pp. 47-50, 2001.

Kondyurin et al., "Plasma immersion ion implantation of polyethylene", Vacuum, vol. 64, pp. 105-111, 2002.

Kondyurin et al., "Pulse and continuous ion beam treatment of polyethylene", Vacuum, vol. 68, pp. 341-347, 2003.

Kutsenko et al., "Structural changes in Mg alloy induced by plasma immersion ion implantation of Ag", Acta Materialia, vol. 52, pp. 4329-4335, 2004.

Prikryl et al., "Mechanical and optical properties of plasma-polymerized vinyltriethoxysilane", Surface and Coatings Technology, vol. 200, pp. 468-471, 2005.

Rao et al., "The characterisation of e-beam evaporated and magnetron sputtered carbon films fabricated for atomic oxygen sensors", Surface & Coatings Technology, vol. 197, pp. 154-160, 2005.

Shiao et al., "Studies of diamond-like and nitrogen-containing diamond-like carbon using laser Raman spectroscopy", Thin Solid Films, vol. 283, pp. 145-150, 1996.

\* cited by examiner

MEDICAL BALLOONS WITH MODIFIED SURFACES

BACKGROUND

This disclosure relates to medical balloons.

The body includes various passageways such as arteries, other blood vessels, and other body lumens. These passageways sometimes become occluded, e.g., by a tumor or restricted by plaque. To widen an occluded body vessel, balloon catheters can be used, e.g., in angioplasty.

A balloon catheter can include an inflatable and deflatable balloon carried by a long and narrow catheter body. The balloon is initially folded around the catheter body to reduce the radial profile of the balloon catheter for easy insertion into the body.

During use, the folded balloon can be delivered to a target location in the vessel, e.g., a portion occluded by plaque, by threading the balloon catheter over a guide wire emplaced in the vessel. The balloon is then inflated, e.g., by introducing a fluid into the interior of the balloon. Inflating the balloon can radially expand the vessel so that the vessel can permit an increased rate of blood flow. After use, the balloon is deflated and withdrawn from the body.

SUMMARY

In an aspect, the invention features a medical device including a generally cylindrical inflatable balloon wall formed of polymer. The balloon wall has a first region of polymer material and a second region where the polymer has a carbonized polymer layer. The first region and second region are arranged in a pattern that facilitates balloon folding into three or more lobes. In an aspect, the invention features a medical device including a generally cylindrical inflatable balloon wall formed of polymer. The balloon wall has a first region of polymer material and a second region where the polymer has an oxidized, carbonized or crosslinked polymer layer with a thickness of 1500 nanometers or less. The second region covers between about 20 and about 50% of the balloon surface and the first region and second region are arranged in a pattern that causes the balloon to fold into a desired configuration.

In an aspect, the invention features a method of treating a medical device, including exposing portions of an inflatable balloon to an ion source, wherein the portions cover between about 20% to about 50% of the balloon surface.

Embodiments of the device may include one or more of the following features. The second region can cover between 10% and 75% of the balloon, such as between about 30% and 50% of the balloon or less than half of the balloon. The second portion can be disposed to the exterior when the balloon is folded. The medical device can include a stent disposed over the balloon. The second region can cover about one third to about one half of the balloon and the second region can be in three separate areas on the balloon that are equidistant from one another along a circumference of the balloon. The second region can be arranged parallel to a center axis of the balloon. Alternatively, the second region the second region can be arranged in a helical pattern, where the angle of the pattern is between a 0 and 45 degrees from a center axis of the balloon. The carbonized polymer layer can be at a depth of between about 1 and 100 nanometers. The carbonized polymer layer can include diamond-like or graphitic material. The stiffer layer of the second region can further comprise one of an oxidized polymer or a crosslinked polymer. The oxidized polymer layer can be directly bonded to the carbonized polymer layer. The second region can include an oxidized polymer layer, the carbonized polymer layer, and a crosslinked polymer layer. The oxidized polymer layer can be on an outer surface of the balloon wall. The oxidized polymer layer can be directly bonded to the carbonized polymer layer. The carbonized polymer layer can have a 500 Vickers Hardness (kgf/mm$^2$) or more. The crosslinked polymer layer can be at a depth of between about 100 and 1500 nanometers. The crosslinked polymer can be directly bonded to the carbonized polymer layer and to a substantially unmodified polymer material. The second region can include the polymer material adjacent to an inner diameter of the balloon wall. The desired configuration can be a folded balloon with at three, four, five or more wings. The balloon can be folded into a desired folded configuration prior to the exposing step, and the exposing step can include exposing an exterior surface of the balloon to the ion source when the balloon is in the desired folded configuration. Exposing the balloon can include one or more of oxidizing material on a surface of the portions, carbonizing material adjacent to the oxidized material or cross-linking material adjacent to the carbonized material. Exposing the portions may not change material at an inner diameter of the balloon. The balloon can be exposed linearly or helically along the length of the balloon. The balloon can be exposed through a mask. The balloon can be inflated prior to the exposing step. The balloon can be exposed to positively charged ions. The balloon can be exposed to about 20 keV of energy.

Advantages of the techniques and devices described herein may provide none, one or more of the following advantages. A balloon with selectively modified regions can fold into a desired configuration, which is in part determined by the location of the modified regions. A balloon that folds into a series of lobes after expansion and deflation within a lumen can have a smaller profile than a similar balloon that does not fold in a similar manner. A folded balloon with a smaller profile can be easier to remove from a lumen than a convention balloon. Moreover, the folded balloon may be less likely to cause complications in a patient and may be safer for use on a patient. The modified, folded balloon can provide a surface more resilient to abrasion or other damage during use.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
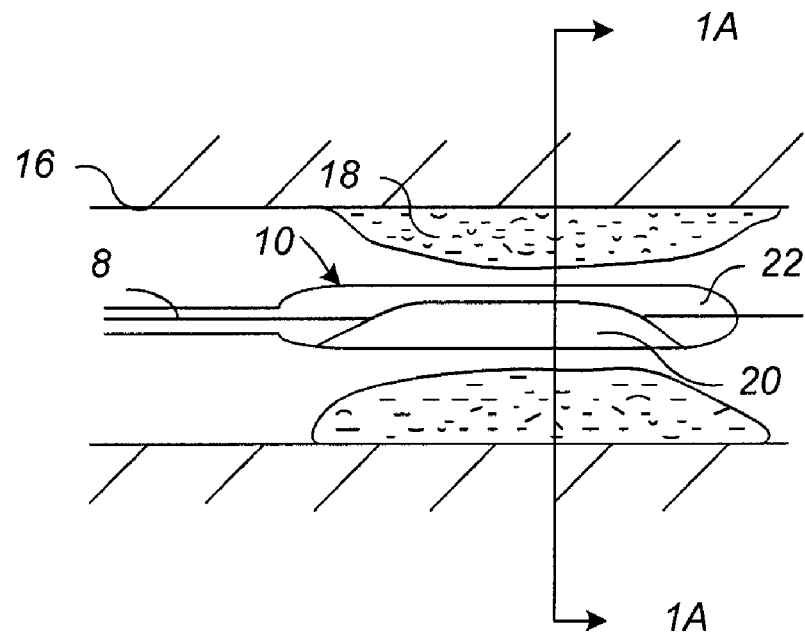
FIG. 1 is a cross sectional view, illustrating a balloon in a folded state within an occluded vessel.
Figure 1A:
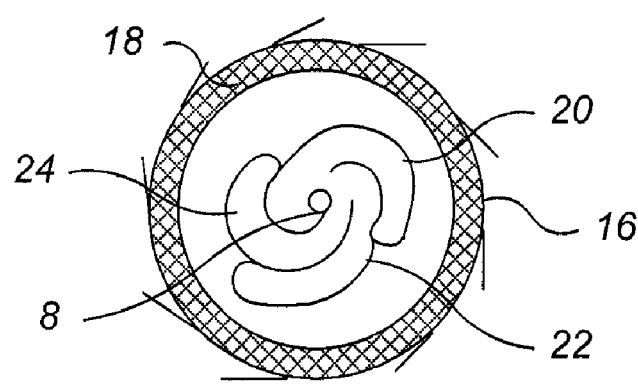
FIG. 1A is an end view of the balloon in the vessel.
Figure 2:
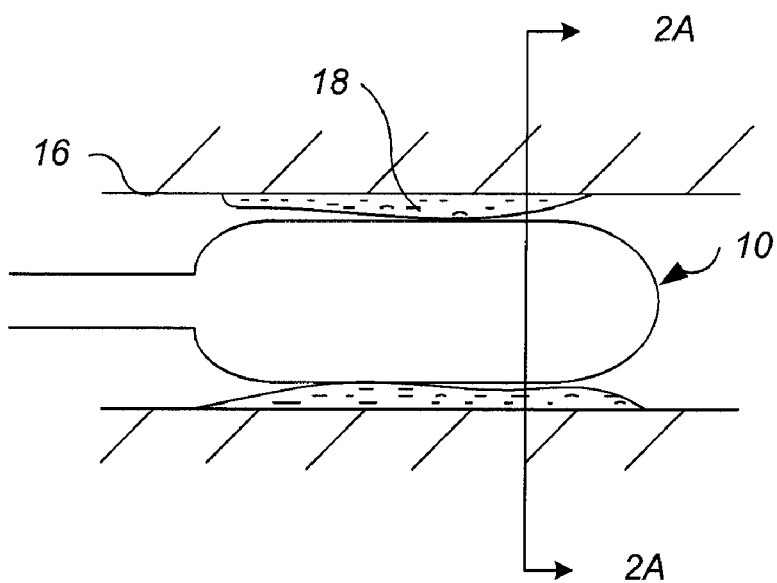
FIGS. 2 and 2A illustrate the balloon in an expanded state.
Figure 2A:
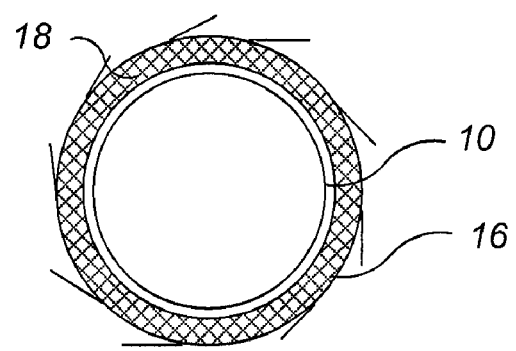
Figure 3:
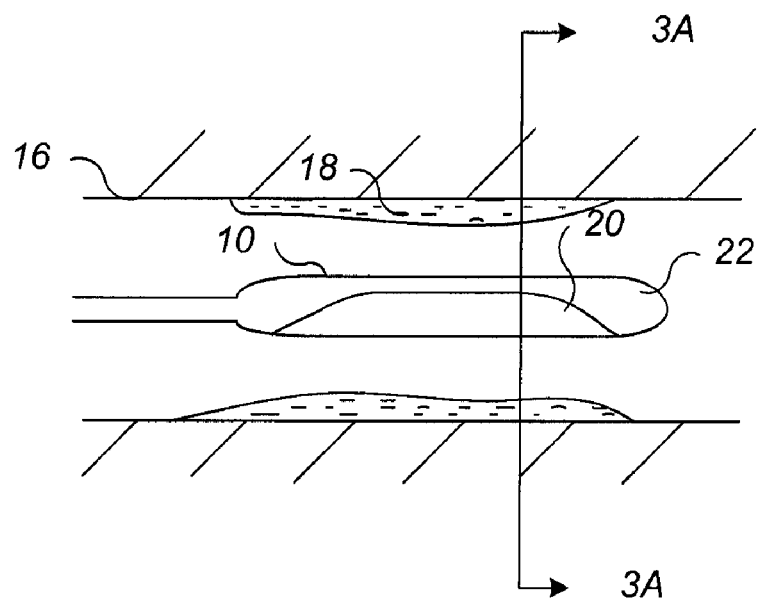
FIGS. 3 and 3A illustrate the balloon in a refolded state.
Figure 3A:
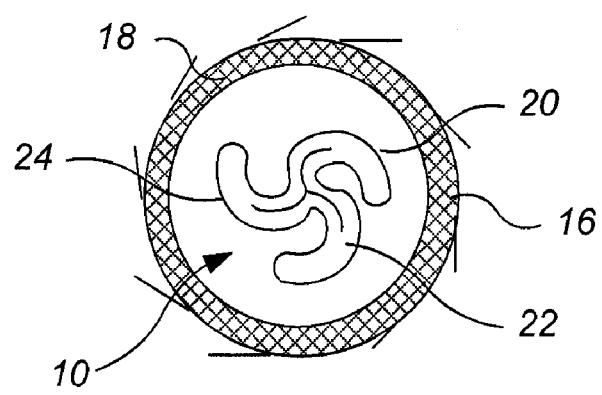

Referring to FIGS. 1 and 1A, a catheter 8 carrying a balloon 10 is directed through a lumen 16 of a body, e.g., a blood vessel such as the coronary artery, e.g. over a guidewire (not shown) until the balloon 10 reaches the region of an occlusion 18. To reduce the cross-sectional profile, the balloon 10 is arranged into a series of lobes or wings 20, 22, 24 which are wrapped about the catheter 10. Referring to FIGS. 2 and 2A, the balloon is then radially expanded by inflating with an inflation fluid. Inflating the balloon 10 causes the walls of the balloon to press against the vessel wall of the lumen 16 with the result that the occlusion 18 is compressed, and the vessel wall surrounding it undergoes a radial expansion. In embodiments, a stent (not shown) is positioned over the balloon and expanded by inflating the balloon. Referring to FIGS. 3 and 3A, as the pressure is released from the balloon 10, the balloon reforms or forms into three lobes, which curl over one another to configure the balloon 10 into a compact shape, which can easily be removed from the lumen 16.

Figure 4:
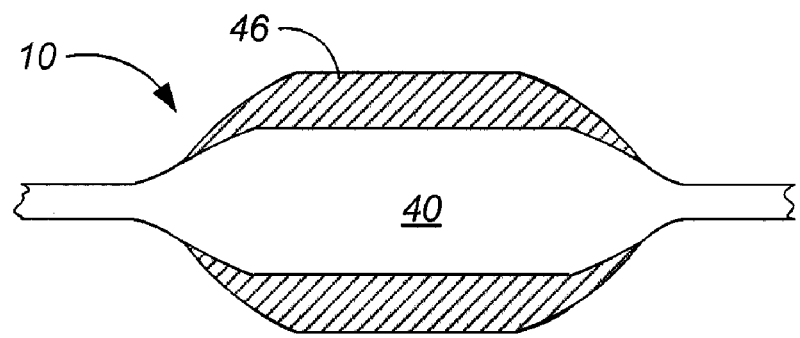
FIG. 4 is a side view of an expanded balloon that has been modified.
Figure 5:
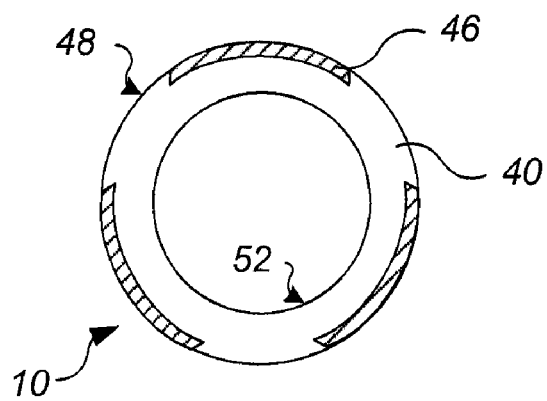
FIG. 5 is a cross sectional view of the modified expanded balloon.

Referring to FIGS. 4 and 5, the balloon has a polymer body with unmodified regions 40 and modified regions 46 that facilitate formation of lobes upon deflation. The modified regions 46 are stiffer than the unmodified regions 40. As will be discussed below, the modified regions preferably are formed by plasma immersion ion implantation such that they include a carbonized zone of the balloon polymer that does not substantially affect balloon properties such as burst strength. That is, the carbonized zone does not prevent the balloon from performing a desired function, such as expansion to a desired burst strength. The modified regions 46 can be located at positions corresponding to a substantial area of the balloon surface, such as between about 10% and 75%, between about 30% and 60% or between about 20% and 50% of the balloon surface. As shown in this embodiment, the modified regions 46 cover about one third of the outer surface 48.

Referring particularly to FIG. 5, a cross section of the balloon 10 shows that in some embodiments, the modified region 46 is located in regions corresponding to an outer surface 48, but does not extend through the thickness to the inner surface 52 or inner diameter of the balloon. That is, the inner diameter 52 of the balloon 10 can include predominately unmodified polymer. In embodiments, the modified region has a thickness of about 10% or less, e.g., about 1% or less or 0.1% or less than the balloon wall thickness.

Figure 6:
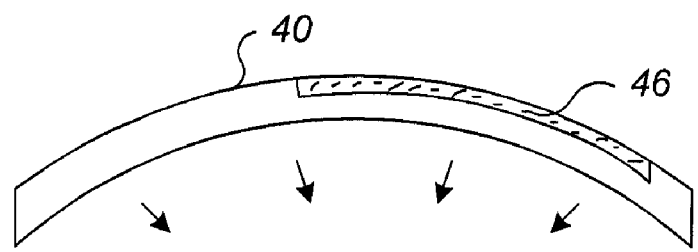
FIGS. 6, 6A and 6B are cross-sectional views of a portion of a balloon during folding.
Figure 6A:
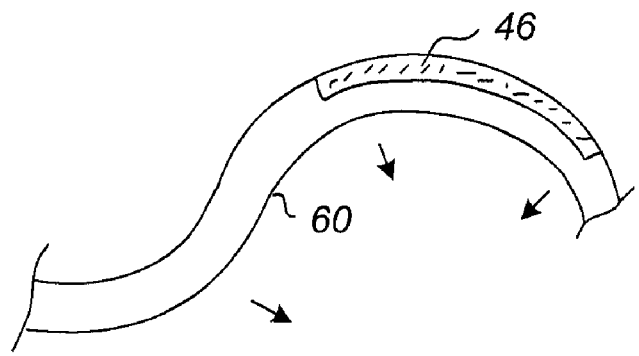
Figure 6B:
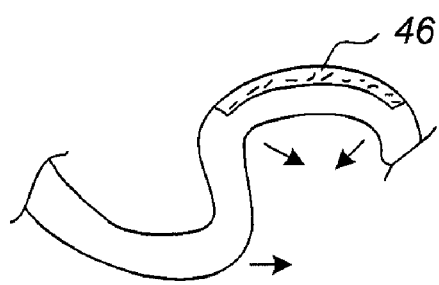

Referring to FIG. 6, the deflated configuration is determined by the pattern of the modified portions 46. As inflation fluid is withdrawn, the unmodified portions 40 deform before the modified regions 46, because of the difference in flexibility between the two portions (FIG. 6A). The unmodified region 40 bends to form valleys 60 between the flaps (FIG. 6B). The flaps form so that the modified regions 46 are on the exterior of the folded balloon. It is an advantage that the stiffness modified regions are on the exterior since these regions can be made more resistant to damage by abrasion with the lumen wall or a stent carried by the balloon. However, in some embodiments, the modified portions 46 are on the interior of the balloon.

The modified regions can be arranged to form two or more, preferably three or more lobes or wings, etc., four, five or more lobes. In addition, while the balloon can have modified and unmodified regions as discussed above, in other embodiments, the entire balloon has been modified but different regions are modified so that they are stiffer than other modified regions.

Figure 7:
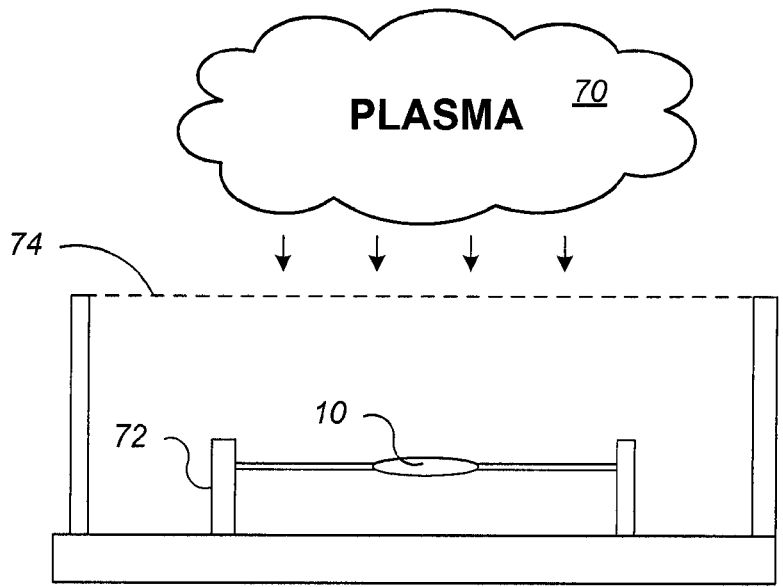
FIG. 7 is a schematic of a plasma immersion ion implantation apparatus.

Referring to FIG. 7, a balloon can be treated ion implantation in a folded configuration to form the modified regions. The unmodified balloon can be formed of a polymer that has substantially consistent properties between an inner diameter and an outer diameter. The balloon can be modified using plasma immersion ion implantation ("PIII"). During PIII, charged species in a plasma 70, such as a nitrogen plasma at about 20 keV, are accelerated at high velocity towards a balloon 10 that is in a folded state, and which is positioned on a sample holder 72. Acceleration of the charged species of the plasma towards the balloon is driven by an electrical potential difference between the plasma and an electrode under the balloon. Upon impact with a balloon, the charged species, due to their high velocity, penetrate a distance into the balloon and react with the material of the balloon, forming the modified regions discussed above. Generally, the penetration depth is controlled, at least in part, by the potential difference between the plasma and the electrode under the balloon and treatment time. Because the balloon is folded during PIII, only the portions that are exposed or on the exterior of the folded balloon are bombarded by the ions. As an alternative to folding the balloon during PIII, a mask can be used to shield portions of the balloon that are to remain untreated, as described further herein. If desired, an additional electrode, e.g., in the form of a metal grid 74 positioned above the sample holder, can be utilized. Such a metal grid 74 can be advantageous to prevent direct contact of the balloons with the rf-plasma between high-voltage pulses and can reduce charging effects of the balloon material. A PIII processing system is described further in U.S. application Ser. No. 11/355,392, "Medical Balloons and Methods of Making the Same", filed on Feb. 16, 2006, the entire contents of which is hereby incorporated by reference.

Figure 8:
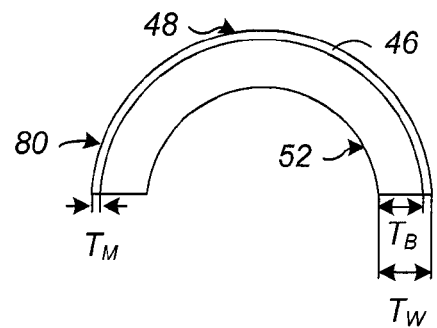
FIG. 8 is a cross sectional view of a wall of the balloon, showing modified and unmodified polymer regions.

Referring to FIG. 8, in some embodiments, the balloon has a wall 80 having overall thickness $T_W$ including an outer surface 48 and an inner surface 52, which is exposed to inflation fluid in the balloon interior. The balloon wall is formed of a base polymer system including an unmodified region 40 and a hard, modified region 46 of thickness $T_M$. The unmodified base polymer has a thickness $T_B$ that is the difference between the overall wall thickness $T_W$ and thickness $T_M$ of the modified region.

Figure 9:
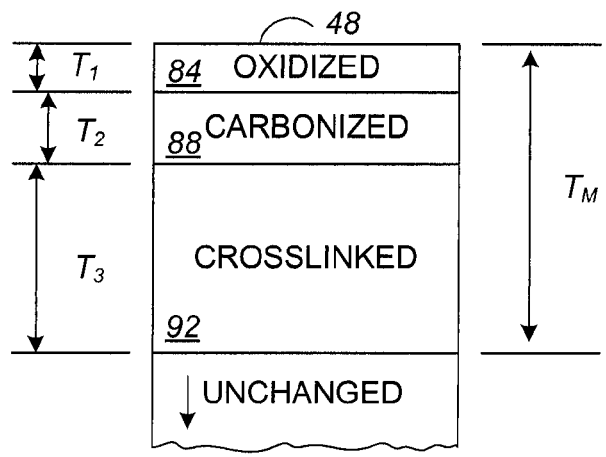
FIG. 9 is a schematic illustration of a compositional makeup of a portion of the balloon wall illustrated in FIG. 8.

Referring to FIG. 9, the modified region has a series of sub-regions, including an oxidized region 84 (e.g., having carbonyl groups, aldehyde groups, carboxylic acid groups and/or alcohol groups), a carbonized region 88 (e.g., having increased $sp^2$ bonding, particularly aromatic carbon-carbon bonds and/or $sp^3$ diamond-like carbon-carbon bonds), and a crosslinked region 92. In particular embodiments, the crosslinked region 92 is a region of increased polymer crosslinking that is bonded directly to the unmodified base polymer system and to the carbonized region 88. The carbonized region 88 is a band that typically includes a high-level of $sp^3$-hybridized carbon atoms, e.g., greater than 25 percent $sp^3$, greater than 40 percent, or even greater than 50 percent $sp^3$-hybridized carbon atoms, such as exists in diamond-like carbon (DLC). The oxidized region 84 that is bonded to the carbonized layer 88 and exposed to atmosphere includes an enhanced oxygen content, relative to the base polymer system. The carbonized region has a hard, scratch resistant nature. The graduated multi-region structure of the modified region enhances adhesion of the modified layer to the unmodified base polymer, reducing the likelihood of delamination. In addition, the graduated nature of the structure and low thickness of the modified region relative to the overall wall thickness enables the balloon to substantially maintain mechanical properties of the unmodified balloon.

The presence of various regions, e.g., carbonized regions, oxidized regions, and crosslinked regions, can be detected using, e.g., infrared, Raman and UV-vis spectroscopy. For example, Raman spectroscopy measurements are sensitive to changes in translational symmetry and are often useful in the study of disorder and crystallite formation in carbon films. In Raman studies, graphite can exhibit a characteristic peak at 1580 $cm^{-1}$ (labeled 'G' for graphite). Disordered graphite has a second peak at 1350 $cm^{-1}$ (labeled 'D' for disorder), which has been reported to be associated with the degree of $sp^3$ bonding present in the material. The appearance of the D-peak in disordered graphite can indicate the presence in structure of six-fold rings and clusters, thus indicating the presence of $sp^3$ bonding in the material. XPS is another technique that has been used to distinguish the diamond phase from the graphite and amorphous carbon components. By deconvoluting the spectra, inferences can be used to determine the type of bonding present within the material. This approach has been applied to determine the $sp^3/sp^2$ ratios in DLC material (see, e.g., Rao, *Surface & Coatings Technology* 197, 154-160, 2005, the entire disclosure of which is hereby incorporated by reference herein). Further discussion of treated balloon characterization is provided in U.S. Ser. No. '392 incorporated supra.

In embodiments, the thickness $T_M$ of the modified region 46 is less than about 1500 nm, e.g., less than about 1000 nm, less than about 750 nm, less than about 500 nm, less than about 250 nm, less than about 150 nm, less than about 100 nm or less than about 50 nm. In embodiments, the oxidized region 84 can have a thickness $T_1$ of less than about 5 nm, e.g., less than about 2 nm or less than about 1 nm. In embodiments, the carbonized region 88 can have a thickness $T_2$ of less than about 500 nm, e.g., less than about 350 nm, less than about 250 nm, less than about 150 nm or less than about 100 nm, and can occur at a depth from outer surface 48 of less than 10 nm, e.g., less than 5 nm or less than 1 nm. In embodiments, the crosslinked region 92 has a thickness $T_3$ of less than about 1500 nm, e.g., less than about 1000 nm, or less than about 500 nm, and can occur at a depth from outer surface 22 of less than about 500 nm, e.g., less than about 350 nm, less than about 250 nm or less than about 100 nm.

In embodiments, the thickness $T_M$ of the modified region is about 10% or less, e.g., about 1% or less, e.g. about 0.5% or less or about 0.05% or more, of the thickness $T_B$ of the unmodified base polymer system. In embodiments, the balloon can be modified to vary the mechanical properties of the polymer or the balloon performance. For example, a balloon stiffness can be enhanced by modifying the balloon to include a relatively thick carbonized or crosslinked layer. In embodiments, the thickness $T_M$ of the modified layer can be about 25% or more, e.g. 50 to 90% of the overall thickness $T_B$ of the unmodified base polymer system. In embodiments, the wall has an overall thickness of less than about 0.005 inch, e.g., less than about 0.0025 inch, less than about 0.002 inch, less than about 0.001 inch or less than about 0.0005 inch.

The type and depth of modification is controlled in the PIII process by selection of the type of ion, the ion energy and ion dose. In embodiments, a three sub-region modification as described above is provided. In other embodiments, there may be more, or less than three sub-regions formed by controlling the PIII process parameters, or by post processing to remove one or more layers by, e.g., solvent dissolution, or mechanically removing layers by cutting, abrasion, or heat treating. In particular, a higher ion energy and dose enhances the formation of carbonized regions, particularly regions with DLC or graphitic components. In embodiments, the ion energy is about 5 keV or greater, such as 25 keV or greater, e.g. about 30 keV or greater and about 75 keV or less. The ion dosage in embodiments is in the range of about $1 \times 10^{14}$ or greater, such as $1 \times 10^{16}$ ions/$cm^2$ or greater, e.g. about $5 \times 10^{16}$ ions/$cm^2$ or greater, and about $1 \times 10^{19}$ ions/$cm^2$ or less. The oxidized region can be characterized, and the process conditions modified based on FTIR ATR spectroscopy results on carbonyl group and hydroxyl group absorptions. Also, the crosslinked region can be characterized using FTIR ATR spectroscopy, UV-vis spectroscopy and Raman spectroscopy by analyzing C=C group absorptions, and the process conditions modified based on the results. In addition, the process conditions can be modified based on an analysis of gel fraction of the crosslinked region, which can be determined using the principle that a crosslinked polymer is not soluble in any solvent, while a non-crosslinked polymer is soluble in a solvent. For example, the gel fraction of a sample can be determined by drying the sample in a vacuum oven at 50° C. until a constant weight is achieved, recording its initial dry weight, and then extracting the sample in a boiling solvent such as o-xylene for 24 hours using, e.g., a Soxhlet extractor. After 24 hours, the solvent is removed from the insoluble material, and then the insoluble material is further dried in a vacuum oven at 50° C. until a constant weight is achieved. The gel fraction is determined by dividing the dry weight of the insoluble material by the total initial dry weight of a sample.

Figure 10:
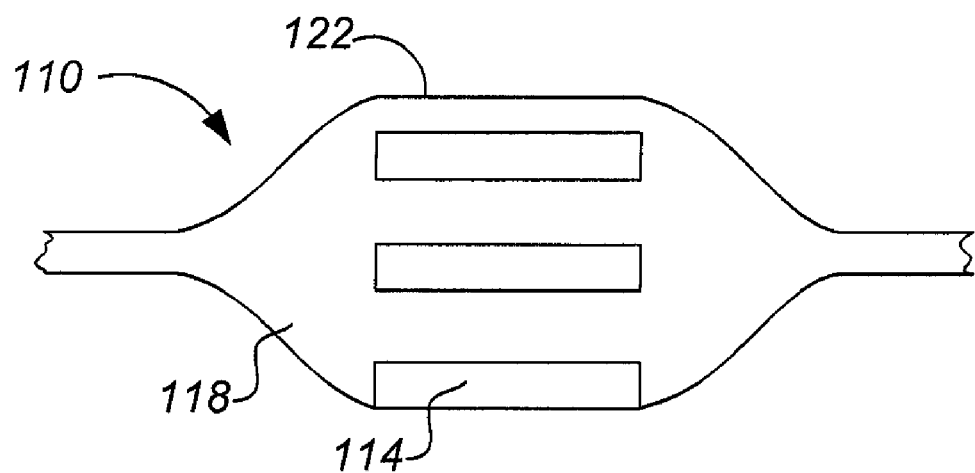
FIG. 10 shows and exemplary pattern of modified regions on a surface of the balloon.
Figure 11:
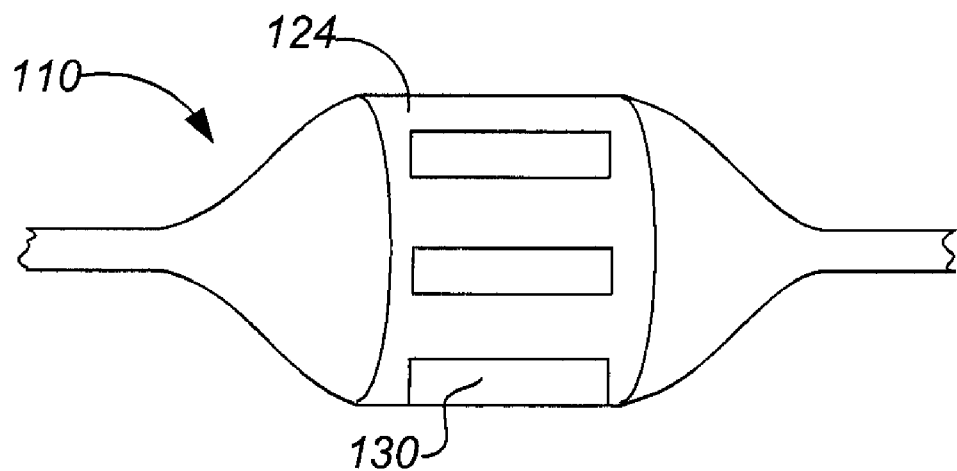
FIG. 11 shows a mask for forming a pattern of modified regions on the balloon.

Referring to FIG. 10, a balloon 110 is treated to have a linear pattern 114 of modified regions on the balloon surface along the balloon body 122. As shown, the modified regions do not extend onto the cones 118 of the balloon 110. The linear pattern 114 can be formed using a mask 124 (FIG. 11). The balloon 110 is placed within the mask 124 and inflated. The mask has apertures 130 through which the balloon is exposed through the mask 114. The balloon is then treated with PIII, as described above. The mask can be formed from a dielectric material, plastic or any material that is suitable for preventing ions from contacting the surface of a balloon within the mask 124.

Figure 12:
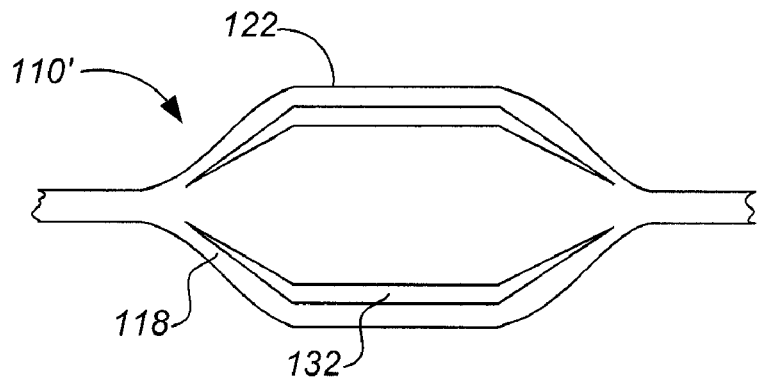
FIGS. 12-14 show alternative modified patterns on balloons.
Figure 13:
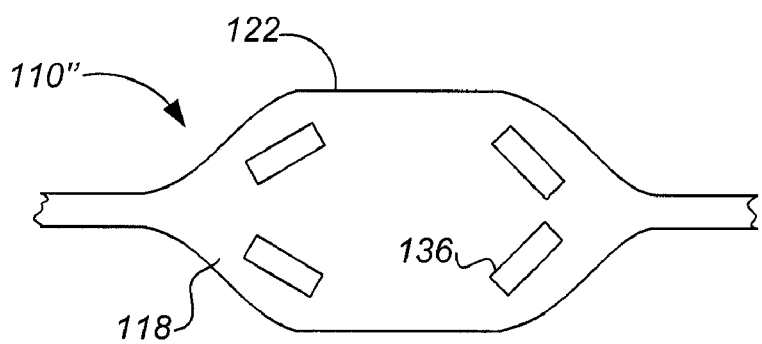
Figure 14:
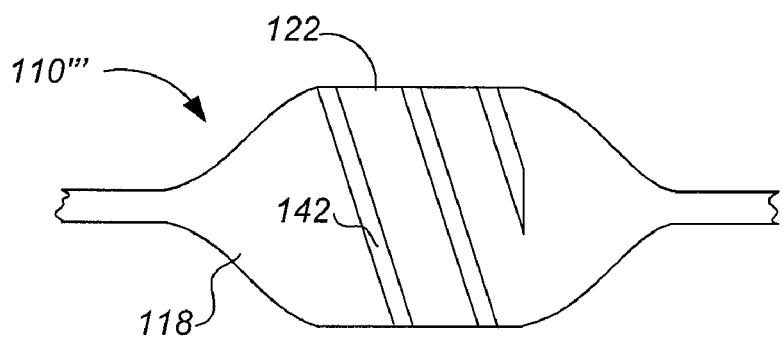

Referring to FIGS. 12-14, additional patterns of modified regions can be formed on the balloon, depending on the desired folding configuration and material that the balloon is formed from. In one embodiment modified region 132 extends along the body 122 of the balloon 110' and onto the cones 118 (FIG. 12). The modified region 132 is substantially linear 132 along the body 122. In one embodiment, conical modified regions 136 are formed only on the cones 118 of the balloon 110" (FIG. 13). In yet another embodiment, helical modified regions 142 wrap around the body 122 of the balloon 110''' (FIG. 14). The helical or spiral modified areas can be at an angle from the center of the balloon 110''', such as an angle between about 0° and 60°, or between about 10° and 50°, or about 45°. When the balloon with helical modified regions 142 folds, the balloon 110''' tends to twist. The regions 132, 136, 142 can be equidistant from one another or vary in distance from one another, depending on the desired folding configuration. The modified regions can have a different width at the ends of the body, that is, close to the cones, than at a center of the body. The modified regions at the ends can be wider or narrower than the modified regions near the center of the body. Combinations of any of the modified regions can be used on a single balloon to achieve the desired folded configuration.

In particular embodiments, the balloon is sized for use in the vascular system, such as the coronary arteries for angioplasty and/or stent delivery. The balloon has a burst strength of about 5 bar or more, e.g., about 15 bar or more. The base polymer system is, e.g., a polymer, a polymer blend, or layer structure of polymer that provides desirable properties to the balloon. In particular embodiments, the base polymer includes a low distendibility, high burst strength polymer. Polymers include biaxially oriented polymers, thermoplastic elastomers, engineering thermoplastic elastomers, polyethylenes, polyethylene terephthalate (PET), polybutylenes, polyamides (e.g. nylon 66), polyether block amides (e.g., PEBAX®), polypropylene (PP), polystyrene (PS), polyvinyl chlorides (PVC), polytetrafluorethylene (PTFE), polymethylmethacrylate (PMMA), polyimide (e.g., nylon 12), polypropylene (PP), polyethylene (PE), polycarbonate (PC), polyisoprene rubber (PI), nitrile rubbers, silicone rubbers, ethylene-propylene diene rubbers (EPDM), butyl rubbers (BR), thermoplastic polyurethanes (PU) (e.g., those based on a glycol ether and an isocyanate, such as PELLETHANE®). In particular embodiments, a poly(ether-amide) block copolymer having the general formula

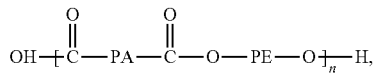

in which PA represents a polyamide segment, e.g., nylon 12, and PE represents a polyether segment, e.g., poly(tetramethylene glycol) is utilized. Such polymers are commercially available from ATOFINA under the tradename PEBAX®.

In particular embodiments, the balloon can have three or more layers, e.g., five, seven or more layers, e.g., with all or just some of the layers being modified. In some embodiments only the out layer or outer layers are modified. In other embodiments, only the innermost layer or inner layers are modified. Balloons formed of coextruded polymer layers are described in Wang, U.S. Pat. Nos. 5,366,442 and 5,195,969, Hamlin, U.S. Pat. No. 5,270,086, and Chin, U.S. Pat. No. 6,951,675, the entire contents of each of which is hereby incorporated by reference herein.

Balloon modification is controlled to produce a desired type of modification at a selected depth. The depth of ion exposure determines the depth of modification. The nature and depth of the modification is also controlled to adjust the overall mechanical properties of the balloon. In particular embodiments, the modification is controlled so that the mechanical properties, such as tensile strength, elongation and modulus of elasticity of the base polymer system are not substantially changed by the presence of the modification. In embodiments, the tensile strength, elongation and modulus of elasticity of the modified polymer is substantially the same as or greater than those respective values of the unmodified polymer. In addition, the modification is controlled so that the desired folding configuration can be achieved.

In embodiments, the balloon can be used in various vascular or non-vascular applications. Exemplary applications include neuro, arterial, esophageal, or vascular. The balloon can be used in angioplasty procedures and can be used to deliver and expand a stent. Stents and stent delivery is also discussed in U.S. Ser. No. '392, supra, as well as in U.S. application Ser. No. 11/355,368, "Bioerodible Endoprothesis and Methods of Making the Same", filed on Feb. 16, 2006, the entire contents of which is hereby incorporated by reference.

All patents, patent applications and publications represented herein are incorporated by reference in their entirety.

A number of embodiments of the invention have been described. Nevertheless, it will be understood that various modifications may be made without departing from the spirit and scope of the invention. Accordingly, other embodiments are within the scope of the following claims.

What is claimed is:

1. A medical device, comprising: a generally cylindrical inflatable balloon wall formed of polymer, wherein the balloon wall has a balloon surface area, first regions of the balloon surface area in which the polymer material taken radially through the wall of the first regions are not carbonized, and second regions of the balloon surface area where the polymer material taken radially through the wall of the second regions have a carbonized polymer layer and the first regions and second regions are arranged in a pattern that facilitates the balloon folding into three or more lobes, said pattern, when the balloon is inflated, providing the balloon with a cross-section taken through at least a first region and a second region that has a circumference with first regions and second regions spaced around said cross-section circumference, and when the balloon is deflated arranged to provide said first regions folded under said second regions, wherein said second regions in a folded configuration completely cover said first regions of the folded balloon.

2. The medical device of claim 1, wherein the second regions cover between about 10% and about 75% of the balloon surface area.

3. The medical device of claim 2, wherein the second regions cover between about 30% and about 50% of the balloon surface area.

4. The medical device of claim 1, wherein the second regions are arranged parallel to a center axis of the balloon.

5. The medical device of claim 1, wherein the second regions are arranged in a helical pattern, where the angle of the pattern is between about 0 and 45 degrees from a center axis of the balloon.

6. The medical device of claim 1, wherein the carbonized polymer layer is at a depth of between about 1 and 100 nanometers.

7. The medical device of claim 1, wherein the carbonized polymer layer includes diamond-like material.

8. The medical device of claim 1, wherein the carbonized polymer layer includes graphitic material.

9. The medical device of claim 1, wherein the second region comprises a layer of material stiffer than the first region material and further comprises one of an oxidized polymer or a crosslinked polymer.

10. The medical device of claim 1, wherein the second region includes an oxidized polymer layer, the carbonized polymer layer, and a crosslinked polymer layer.

11. The medical device of claim 10, wherein the carbonized polymer layer has a 500 Vickers Hardness (kgf/mm$^2$) or more.

12. The medical device of claim 10, wherein the crosslinked polymer layer is at a depth of between about 100 and 1500 nanometers.

13. The medical device of claim 10, wherein the crosslinked polymer is directly bonded to the carbonized polymer layer and to a substantially unmodified polymer material.

14. A medical device, comprising: a generally cylindrical inflatable balloon wall formed of polymer wherein the balloon wall has a balloon surface area, first regions of the balloon surface area in which the polymer material taken radially through the wall of the first regions is not carbonized, and second regions of the balloon surface area where a polymer material taken radially through the wall of the second region has an oxidized, carbonized, or crosslinked polymer layer with a thickness of 1500 nanometers or less, the second regions cover between 20% and 50% of the balloon surface area and the first regions and second regions are arranged in a pattern that causes the balloon to fold into a folded configuration;

said pattern, when the balloon is inflated, providing the balloon with a cross-section taken through at least a first region and a second region that has a circumference with first regions and second regions spaced around said cross-section circumference, and when the balloon is deflated arranged to provide said first regions folded under said second regions, wherein said second regions in a folded configuration completely cover said first regions of the folded balloon.

15. The medical device of claim 14, wherein the oxidized, carbonized or crosslinked polymer layer has a thickness of between about 1 and 100 nanometers.

16. The medical device of claim 14, wherein the second regions have the carbonized polymer layer.

17. The medical device of claim 14, wherein the second regions have the crosslinked polymer layer.

18. The medical device of claim 14, wherein the second regions include diamond-like material.

19. The medical device of claim 14, wherein the second regions include graphitic material.

20. The medical device of claim 14 wherein the second regions comprise a modified region that has a thickness corresponding to less than 10% of the balloon wall thickness, the remainder of the balloon wall thickness being unmodified polymer.

21. The medical device of claim 14 wherein the balloon wall comprises a generally cylindrical body portion and the first and second regions are on the cylindrical body portion.

22. The medical device of claim 14 wherein the balloon wall comprises a tapered cone region with at least portions of said first and second regions being located on said cone regions.

23. The medical device of claim 1 wherein the balloon wall comprises a generally cylindrical body portion and the first and second regions are at least partially located on the cylindrical body portion.

24. The medical device of claim 1 wherein the balloon wall comprises a tapered cone region with at least portions of said first and second regions being at least partially located on said cone regions.

* * * * *